(12) United States Patent
Platzek et al.

(10) Patent No.: US 8,314,248 B2
(45) Date of Patent: Nov. 20, 2012

(54) PROCESS FOR PREPARING EPOTHILONE DERIVATIVES BY SELECTIVE CATALYTIC EPOXIDATION

(75) Inventors: Johannes Platzek, Berlin (DE); Orlin Petrov, Berlin (DE); Stephan Prühs, Neuss (DE)

(73) Assignee: Bayer Pharma AG, Berlin (DE)

( * ) Notice: Subject to any disclaimer, the term of this patent is extended or adjusted under 35 U.S.C. 154(b) by 0 days.

(21) Appl. No.: 13/308,046

(22) Filed: Nov. 30, 2011

(65) Prior Publication Data

US 2012/0077984 A1 Mar. 29, 2012

(30) Foreign Application Priority Data

Mar. 30, 2007 (DE) .......................... 10 2007 016 046

(51) Int. Cl.
*C07D 417/04* (2006.01)
(52) U.S. Cl. ...................................... 548/159
(58) Field of Classification Search .................. None
See application file for complete search history.

(56) References Cited

U.S. PATENT DOCUMENTS

| | | |
|---|---|---|
| 6,387,927 B1 | 5/2002 | Altmann et al. |
| 2004/0019088 A1 | 1/2004 | Lichtner et al. |

FOREIGN PATENT DOCUMENTS

| | | |
|---|---|---|
| WO | WO 00/66589 | 5/2000 |
| WO | WO 00/37473 A1 | 6/2000 |
| WO | WO 2005/090335 A1 | 9/2005 |

OTHER PUBLICATIONS

K. Altmann et al., "Synthesis and Biological Evaluation of Highly Potent Analogues of Epothilones B and D", Bioorganic & Medicinal Chemistry Letters, vol. 10, (2000) pp. 2765-2768.
F. Cachoux et al., "Entwicklung Struktureller Template Zur Mikrotubulihemmung Durch Weitgehende Abwandlung Der Epothilongrundstruktur", Angew. Chem., vol. 117, (2005) pp. 7636-7640.
International Search Report of PCT/EP2008/002652 (Dec. 9, 2008).
U. Klar et al., "Total Synthesis and Antitumor Activity of ZK-EPO : The First Fully Synthetic Epothilone in Clinical Development", Angew. Chem. Int. Ed., vol. 45 (2006) pp. 7942-7948.
F. E. Kuhn et al., "Methyltrioxorhenium and Its Applications in Olefin Oxidation, Metathesis and Aldehyde Olefination", Journal of Organometallic Chemistry, vol. 689 (2004) pp. 4149-4164.

*Primary Examiner* — Laura L. Stockton
(74) *Attorney, Agent, or Firm* — Millen, White, Zelano & Branigan, P.C.

(57) ABSTRACT

The present invention describes a novel process for preparing an epothilone derivative using substituted pyridines and methyltrioxorhenium as catalyst.

10 Claims, No Drawings

PROCESS FOR PREPARING EPOTHILONE DERIVATIVES BY SELECTIVE CATALYTIC EPOXIDATION

This application claims the benefit of the filing date of U.S. Provisional Application Ser. No. 60/907,415 filed Apr. 2, 2007.

The invention relates to the subject-matter characterized in the claims, that is to say a novel selective epoxidation process for preparing the epothilone derivative of the formula I. The process of the invention affords the target compound of the formula I in high chemical and diastereomeric purity, very good yields and permits preparation on a large scale.

Höfle et al. described the cytotoxic effect of the natural products epothilone A (R=hydrogen) and epothilone B (R=methyl)

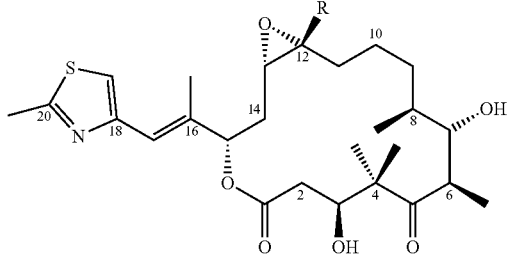

Epothilone A (R=H), Epothilone B (R=CH₃)

e.g. in Angew. Chem. 1996, 108, 1671-1673. Epothilones are representatives of a class of promising antitumour agents which have been tested as potent against a number of cancer lines. An overview of the syntheses have been described for example by J. Mulzer in *Monatsh. Chem.* 2000, 131, 205-238. These agents display the same biological mechanism of action as paclitaxel and other taxanes (concerning paclitaxel, see D. G. I. Kingston, *Chem, Commun.* 2001, 867-880). Epothilones differ from the latter by being active against a number of resistant cell lines (see S. J. Stachel et al., *Curr. Pharmaceut. Design* 2001, 7, 1277-1290; K.-H. Altmann, *Curr. Opin. Chem. Biol.* 2001, 5, 424-431).

Because of the in vitro selectivity in relation to breast and bowel cell lines and their distinctly higher activity, compared with Taxol, against p-glycoprotein-forming, multiresistent tumour lines, and their improved physical properties, compared with Taxol, e.g. a solubility in water which is a factor of 30 higher, this novel structural class is of particular interest for developing a medicament for the therapy of malignant tumours.

A whole series of synthetically modified epothilone derivatives have been prepared, including those having an aromatic or heteroaromatic group in position 1 instead of the methylthiazole-methylvinyl side chains.

Epothilone derivatives with fused aromatic heterocycles in position 1 are disclosed in the patent literature, e.g. by Schering AG, WO 00/66589 and Novartis WO 2000/037473. Since these compounds are very potent antitumour agents, it is of great interest to have an economic and efficient synthesis of this structural class available.

Among the compounds described in the Schering application WO 00/66589, compound (I) was particularly notable:

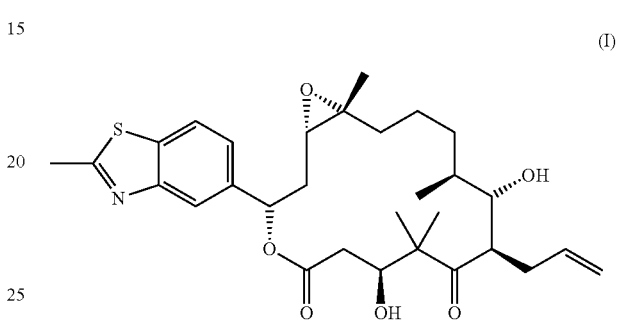

Because of the outstanding data from animal experiments, this compound was selected for development. The compound is currently undergoing clinical trials. The synthesis is described in Angewandte Chemie, Int. Ed. (2006), 45 (47), 7942.

There was a great need for a selective method for epoxidizing the trisubstituted double bond in position 12,13

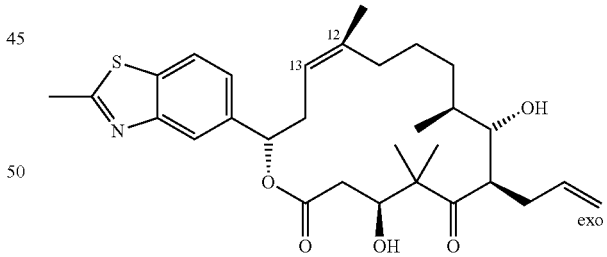

because there is observed to be with the processes described in the prior art (see below) firstly a relatively moderate selectivity (averaging 7-10:1 alpha/beta epoxide) and an additional attack of the epoxidizing reagent on the exo double bond.

Epoxidation of the exo double bond leads in an immediately following reaction to the unwanted impurities mentioned below (IIIa+IIIb). These impurities may arise from the product of the formula (by overoxidation) or else even from the alkene II:

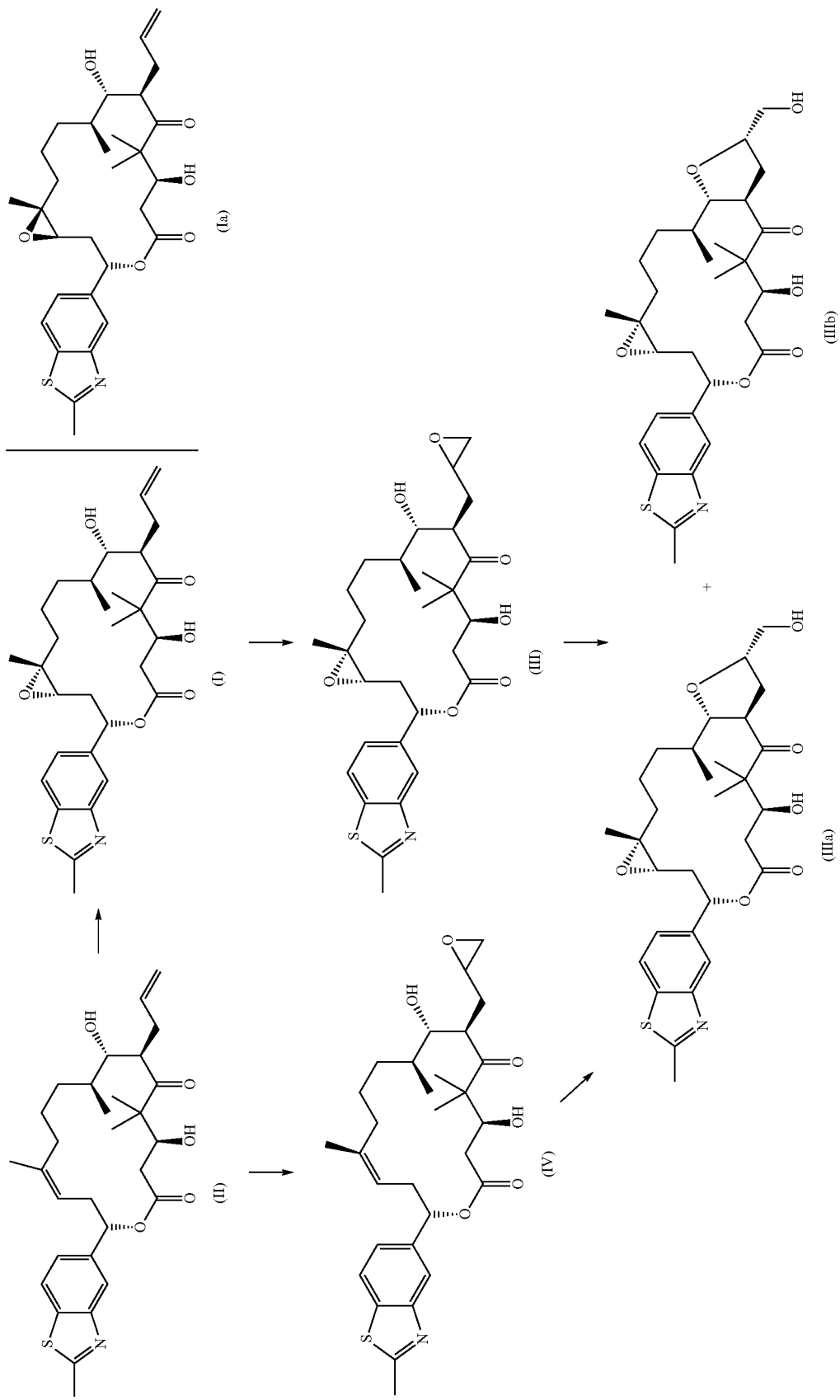

Because of the moderate selectivity of the epoxidation methods described, the reaction mixture contains besides the target compound I also the beta isomer (Ia), from which corresponding impurities likewise arise in an analogous manner. Removal of all these by-products is time-consuming and takes place by difficult, elaborate and costly chromatography.

Numerous methods for epoxidizing epothilones have now been published. The epoxidizing agents described in the literature for epoxidizing epothilone derivatives are substantially those mentioned below:

| Reagent | Literature | Yields (selectivities) |
|---|---|---|
| DMDO (2,2-Dimethyldioxirane) | JACs, 2001, 5407 | 78% |
| | JACS 2000, 10521 | 97% |
| | Tetrahedron Lett. 2001, 6785 | 100% |
| | JACS, 1999, 7050 | 80% |
| | Angewandte Chemie, 1998, 2821 | 98% |
| | JOC, 1999, 684 | 78% |
| 2-Trifluoromethyl-2-methyldioxirane | Chem. Comun. 1997, 2343 | 20%/55% |
| | Chem. Eur. J., 1997, 1971 | 76% (8:1) |
| Review on the reagent: Acc. Chem. Rev. 2004, 37, 497-505 | | 60% (2:1) |
| | JACS, 2001, 5249 | 60% |
| | Org. Lett. 2001, 3607 | 56% |
| | JACS, 1997, 7974 | 85% (5:1) |
| MCPBA (Meta-chloroperbenzoic acid) | JACS, 1997, 7974 | 66% (5:1) |
| | Chem. Europ. J. 1997, 1971 | 34%/38% |
| | Org. Biomol. Chem. 2004, 127 | 55% |
| | Org, Lett. 2001, 2221 | 65% |
| Shi catalyst/Oxone | Angew. Chem. 2005, 117, 7636 | 65% (5:1) |
| Review: synthesis, 2000, No. 14, 1979-2000 Acc. Chem. Res. 2004, 37, 488-496 | Application to ZK EPO starting from dialkene II | 63% (5:1) |
| Methyltrioxorhenium (MTO) | Angew. Chem. 2005, 117, 7636 and Bioorganic Med. Chem. 10 (2000), 2765 | 9-10:1 |

All these reagents have the disadvantage that, besides a poor α/β selectivity on the epoxide, there is also extensive attack on the exo double bond (in some cases >>5%), which means that the regioselectivity is also unsatisfactory. Extensive losses of yield in the last stage of the synthesis are the result. Since the dialkene (II) itself is very valuable, having been prepared over many stages, the loss of every percent of product in the last step is very uneconomic.

The only practicable method, which has also been transferred to the pilot-plant scale, is the use of dimethyldioxirane (DMDO in acetone) at low temperature and high dilution:

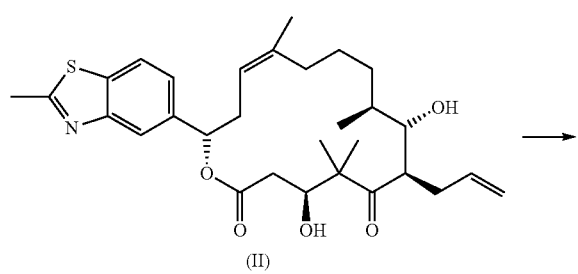

(II)

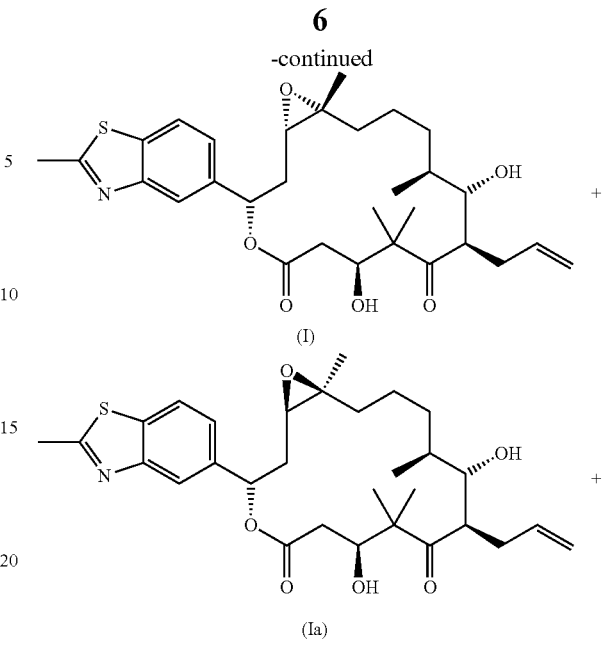

impurities from exo attack

Although relatively high yields are described in many publications (see above), this method is unsatisfactory for our substrate, however. The selectivities achieved in this process were 7-7.6:1 (α/β), and the yields after isolation of the pure compound in the laboratory (small batches) were 71% of theory (after chromatography and crystallization), but were only 64% of theory on the operational scale.

The use of MTO as epoxidation catalyst, also in combination with a wide variety of pyridine derivatives, has been known per se for a long time:

Chem. Eur. J. 2002, 8, No. 13, 3053

Chem. Commun. 200, 1165

Tetrahedron Letters 40 (1999), 3991

JACS 1997, 119, 11536

JACS 1997, 119, 6189

Angew. Chem. Int. Ed. Engl. 30 (1991) No. 12, 1638

JOC 2000, 65, 5001 and 8651

J. Organometallic Chemistry 555 (1998), 293

JACS 1998, 120, 11335

Monograph: "Aziridines and Epoxides in Organic Synthesis", Andrei K. Yudin, Wiley-VCH Verlag GmBH & Co. KGaA 2006, pp. 185-228, and the literature cited therein.

However, the reaction is in most cases carried out at room temperature. It is possible to epoxidize both tri- and di- and monosubstituted double bonds using this method.

However, diastereoselective epoxidations with high selectivities (e.g. on natural products, e.g. of the epothilone type) are not described.

Two publications by Altmann (Angew. Chem. 2005, 117, 7636 and Bioorg. Med. Chem. Lett. 10 (2000), 2765) describe the use of catalytic amounts of methyltrioxorhenium (MTO) in combination with pyridine and hydrogen peroxide (as oxygen source).

These publications by Altmann describe the first application of the MTO reagent for the selective preparation of epothilones:

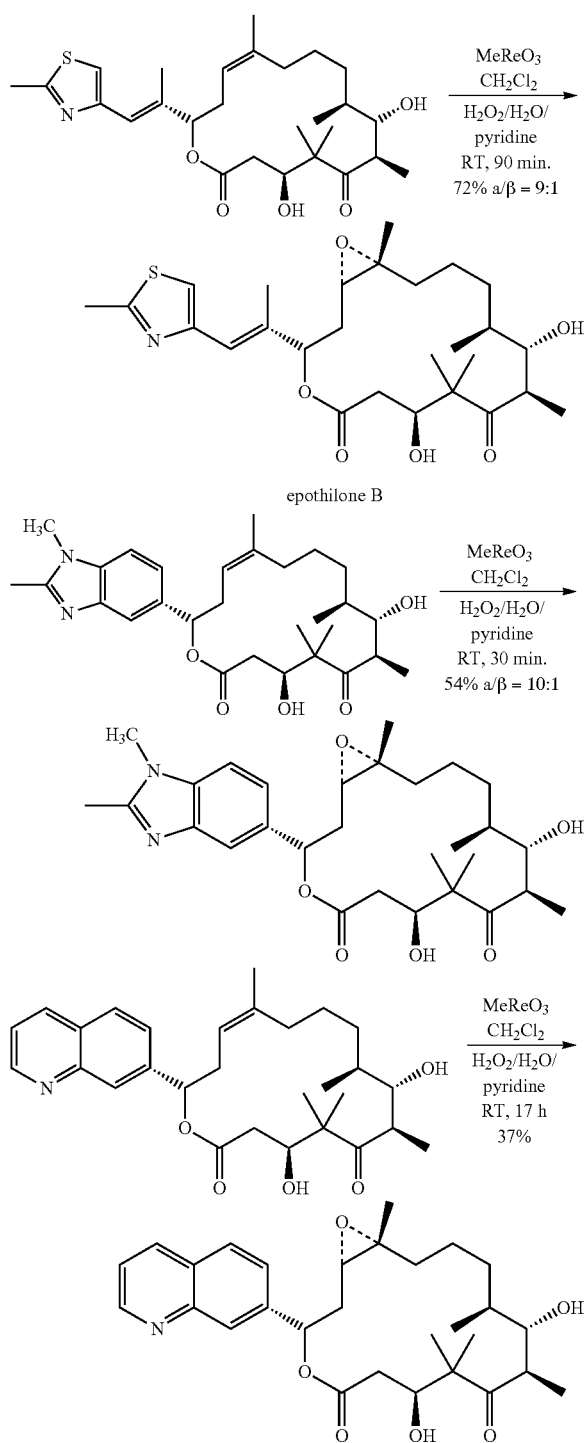

epothilone B

The examples described in these publications contain no additional exo double bonds of the type in the compound of the formula I, but in the case of epothilone B there is an additional double bond which is conjugated with the thiazole ring. However, it is known that this double bond is not attacked by other epoxidizing reagents because of the lower electron density (electron-poor double bond, because conjugated with the aromatic system). The selectivities achieved are in a moderate range, at 9-10:1, with yields of 37-72% of theory. The reactions are carried out at room temperature and prolongation of the reaction time leads to losses of yield.

No reactions with aqueous $H_2O_2$ at low temperatures below $-10°$ C. are described in the prior art, because the skilled person assumes that the reagent freezes under the conditions and is no longer able to react.

However, we have now surprisingly found that reactions still take place even at temperatures down to $-60°$ C., although the reagent is present in the frozen state in the solution.

The attempt to use the Altmann method nevertheless for preparing the compound of the formula I by, for example, lowering the temperature was, however, unsatisfactory because the selectivities were <10:1 ($\alpha/\beta$) in all cases. In addition, the above-mentioned impurities (about 2-4%) were likewise observed. The following table shows the results obtained:

| Temperature | Conversion | Selectivity | Reaction time |
|---|---|---|---|
| $-50°$ C. | 90% | 9.8:1 | 12 h |
| $-40°$ C. | 96% | 9.2:1 | 5 h |
| $-30°$ C. | 99% | 8.6:1 | 5 h |
| $-20°$ C. | 99% | 7.4:1 | 3 h |
| $-10°$ C. | 99% | 6.7:1 | 3 h |
| $0°$ C. | 99% | 6.5:1 | 3 h |
| RT ($20°$ C.) | 99% | 5.1:1 | 3 h |

The results show that the prior art methods are still unsatisfactory for the synthesis of the epothilone derivatives of the formula (I).

It was therefore the object to provide a novel method permitting the epothilone derivative of the formula I to be prepared with high $\alpha/\beta$ selectivity, high regioselectivity, high purity of the crude product, and high yield on the pilot scale so that elaborate chromatographic removal of the by-products described above is avoided.

The present invention achieves this object and describes a novel process for preparing this epothilone derivative of the formula I starting from the dialkene of the formula II which is likewise known from the literature (II)

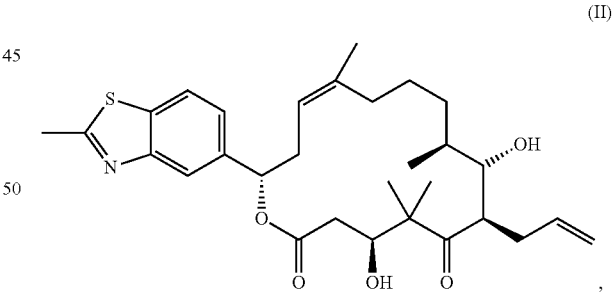

which is obtained with high selectivity by epoxidizing the trisubstituted double bond using methyltrioxo-rhenium in an aprotic solvent at low temperature, in particular at $-60°$ C. to $-20°$ C.

This surprisingly takes place particularly well on use of a combination of methyltrioxorhenium (MTO) with substituted pyridines, especially with 4-cyanopyridine.

Aqueous hydrogen peroxide solution especially in an aprotic solvent at $-60°$ C. to $-20°$ C. is particularly suitable as epoxidizing agent.

The compound of the formula (I) is obtained from the dialkene of the formula II

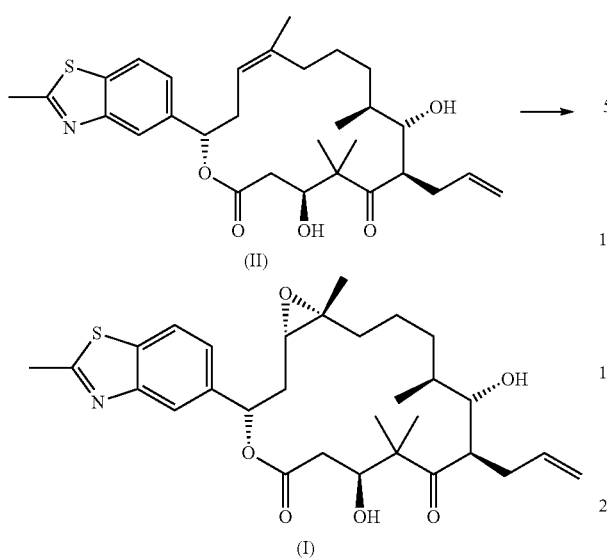

by reaction
  in an aprotic solvent, in particular a chlorinated hydrocarbon, preferably dichloromethane or mixtures thereof with low-boiling alkanes, trifluorotoluene or toluene as solvent
  in concentrations of from 5-fold ("5-fold" means, 1 g of dialkene in 5 ml of solvent) to 50-fold (1 g of dialkene in 50 ml of solvent), preferably 5-20-fold, particularly preferably 10-fold,
  using 6-36 mol %, preferably 10-25 mol %, particularly preferably 18 mol %, of a substituted pyridine, preferably of an electron-poor substituted pyridine, particularly preferably 4-CN-pyridine,
  and 1-7 mol % methyltrioxorhenium, preferably 1-5%, particularly preferably 3 mol %, and
  2-5 equivalents (eq.), preferably 3-4 eq., particularly preferably 3 eq., of 10-60% strength aqueous hydrogen peroxide solution, preferably 30-350,
  at reaction temperatures of from –60° C. to –20° C., preferably at –55° C. to –35° C., particularly preferably at –50° C.,
  with reaction times of 20-120 h, preferably 40-100 h, particularly preferably 50-90 h.

One embodiment of the invention represents the process described above when all the first-mentioned conditions are combined together:
  chlorinated hydrocarbons or mixtures thereof with low-boiling alkanes or toluene or trifluorotoluene as solvent,
  concentration of the dialkene 1 g/5 ml-50 ml
  6-36 mol % of a substituted pyridine,
  1-7 mol % methyltrioxorhenium and
  2-5 equivalents of a 10-60% strength aqueous hydrogen peroxide solution.

A further embodiment relates to a process in which the following conditions are combined together:
  chlorinated hydrocarbons or mixtures thereof with low-boiling alkanes or toluene or trifluorotoluene as solvent,
  concentration of the dialkene 1 g/5 ml-50 ml
  6-36 mol % of a substituted pyridine,
  1-7 mol % methyltrioxorhenium and
  2-5 equivalents of a 10-60% strength aqueous hydrogen peroxide solution
  reaction temperatures of –60° C. to –20° C. and
  reaction times of 20-120 h.

One aspect of the invention represents the process described above when the preferred conditions
  dichloromethane or mixtures thereof with low-boiling alkanes, trifluorotoluene or toluene as solvent
  concentration of the dialkene 1 g/5 ml-20 ml
  10-25 mol % of an electron-poor substituted pyridine,
  1-5% methyltrioxorhenium,
  3-4 equivalents of a 30-35% strength aqueous hydrogen peroxide solution
are combined together.

A further embodiment of the invention represents the process described above when all the preferred conditions are combined together:
  dichloromethane or mixtures thereof with low-boiling alkanes, trifluorotoluene or toluene as solvent
  concentration of the dialkene 1 g/5 ml-20 ml
  10-25 mol % of an electron-poor substituted pyridine,
  1-5% methyltrioxorhenium,
  3-4 equivalents of a 30-35% strength aqueous hydrogen peroxide solution
  reaction temperatures of –55° C. to –35° C. and
  reaction times of 40-100 h.

A further embodiment of the invention represents the process described above when all the particularly preferred conditions are combined together, the intention being if no particularly preferred range is indicated that the preferred range is combined:
  dichloromethane or mixtures thereof with low-boiling alkanes, trifluorotoluene or toluene as solvent
  concentration of the dialkene 1 g/10 ml
  18 mol % of 4-CN-pyridine,
  3 mol % methyltrioxorhenium,
  3 equivalents of a 30-35% strength aqueous hydrogen peroxide solution,
  at reaction temperatures of –50° C. and
  reaction times of 50-90 h.

A particular embodiment of the invention is a process for preparing the compound of the formula (I)

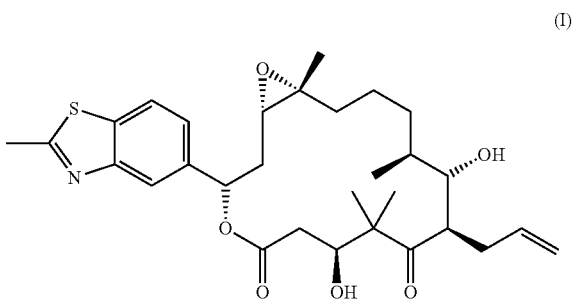

when the dialkene of the formula (II)

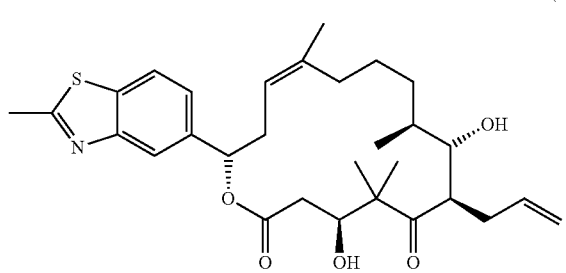

(II)

is reacted in dichloromethane as solvent in concentrations of 1 g of dialkene in 10 ml of solvent, using 18 mol % 4-CN-pyridine,
and 3% methyltrioxorhenium, and 3 eq of 10-60% strength aqueous hydrogen peroxide solution,
at reaction temperatures of from −60° to −20° C.
with reaction times of 50-90 h.

In a particularly preferred embodiment, the process is carried out precisely under the conditions of Example 1.

One embodiment of the invention is one of the processes as described above, in which the reaction temperature is −60° C. to −20° C.

In one embodiment of the invention, the reaction takes place at temperatures of from −55 to −35° C.

A further embodiment is the process as described in Claim 1, in which the reaction times are between 20-120 h.

In one embodiment of the invention, the reaction times are from 40 to 80 h.

In one embodiment of the invention the amount of methyltrioxorhenium is 1-5 mol %, where the amount is based on the dialkene.

A further embodiment is one of the processes as described above, where the concentrations of the compound of the formula II are from 1 g in 5 ml of solvent to 1 g in 50 ml of solvent.

A further embodiment is one of the processes as described above, where the dialkene is present in concentrations of from 1 g in 5 ml of solvent to 1 g in 20 ml of solvent.

It is also possible to use, instead of dichloromethane, other solvents such as 1,2 dichloroethane, chloroform and mixtures thereof with pentane, hexane, heptane, cyclohexane or other low-boiling alkanes in various ratios, and aromatic solvents (arylalkanes) such as, for example, toluene, trifluorotoluene. It is also possible to employ dichloromethane mixed with the abovementioned alkanes and arylalkanes.

Low-boiling alkanes mean straight-chain and branched alkanes and cycloalkanes having boiling points of about 35° C. to 100° C.

In one embodiment of the invention, the solvent is selected from the group of dichloromethane, 1,2-dichloroethane, chloroform, and mixtures thereof with pentane, hexane, heptane, cyclohexane, toluene or trifluorotoluene, or toluene or trifluorotoluene on their own.

In one embodiment of the invention, the solvent is selected from the group of mixtures of dichloromethane with pentane, hexane, heptane, cyclohexane, toluene, or trifluorotoluene.

In a further embodiment of the invention, the solvent is selected from the group of dichloromethane and mixtures of dichloromethane with pentane, hexane, heptane, cyclohexane, toluene, or trifluorotoluene.

Besides 4-cyanopyridine it is also possible to use as alternative pyridine catalysts for example

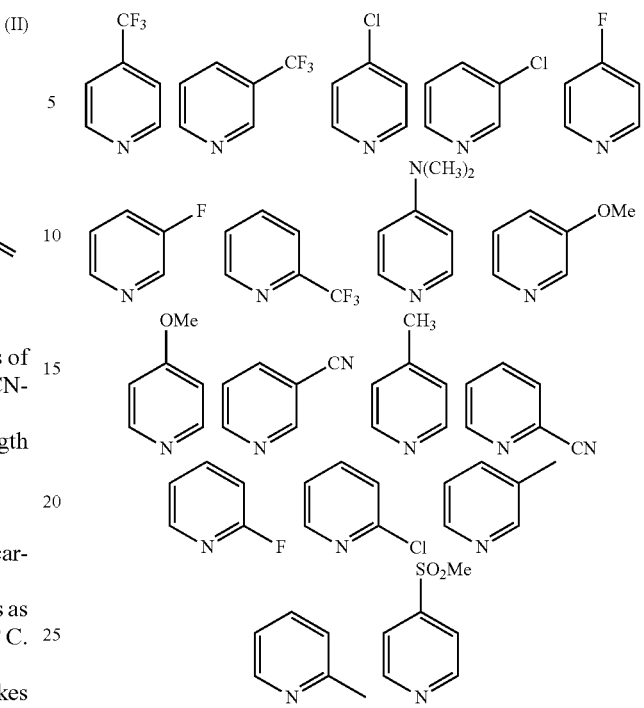

preferably

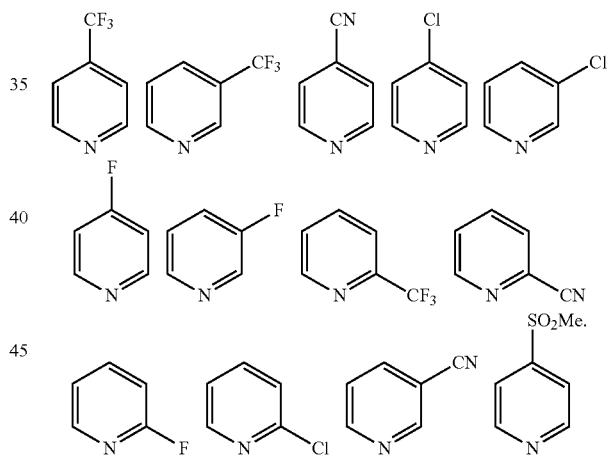

In a further embodiment, 2- or 4-substituted electron-poor pyridine derivatives substituted by CN, Br, Cl, F, $CF_3$, $SO_2(C_1-C_4)$alkyl, $SO_2NH_2$, $SO_2N[(C_1-C_4)$alkyl$]_2$, COOH, COO$(C_1-C_4)$alkyl, in particular pyridines substituted by CN, Cl, F, $SO_2CH_3$, COOH, COO$(C_1-C_4)$alkyl, are employed.

In a preferred embodiment, 4-substituted electron-poor pyridine derivatives substituted by CN, Br, Cl, F, $CF_3$, $SO_2(C_1-C_4)$alkyl, $SO_2NH_2$, $SO_2N[(C_1-C_4)$alkyl$]_2$, COOH, COO$(C_1-C_4)$alkyl, in particular pyridines substituted by CN, Cl, F, $SO_2CH_3$, COOH, COO$(C_1-C_4)$alkyl, are employed.

2- and 4-CN-pyridine is particularly preferred, and 4-CN-pyridine is very particularly preferred.

The term $C_1-C_4$-alkyl means straight-chain or branched, for example methyl, ethyl, propyl, isopropyl.

In one embodiment of the invention, the amount of substituted pyridine is 10-20 mol %, the amount being based on the dialkene.

In one embodiment of the invention, 30-35% strength aqueous hydrogen peroxide solution is employed.

In one embodiment of the invention, 3-4 equivalents of hydrogen peroxide, based on the dialkene, are employed.

It has proved advantageous in some cases to replace hydrogen peroxide by the urea-hydrogen peroxide complex (UHP) (Lit. Angew. Chemie 1991, 103, 1706 and Angew. Chemie, 1996, 108, 578).

One embodiment of the invention therefore relates to a process as defined in Claim 1, where UHP is used as epoxidizing agent.

For workup, a reducing agent known to the skilled person, such as, for example, sodium thiosulphate, sodium sulphite, vitamin C etc., is used to destroy the excess hydrogen peroxide, followed by washing with water, and aqueous acidic solutions (for extractive removal of the pyridine catalyst) of, for example, $KHSO_4$, $H_2SO_4$, HCl, phosphoric acid, methanesulphonic acid, TFA, citric acid in water. A final wash with saturated aqueous NaCl solution is possible where appropriate, followed by drying over magnesium sulphate or sodium sulphate and then removal of the solvent by distillation in vacuo. The residue is purified by chromatography and then the compound of the formula (I) is finally purified by crystallization and isolated. However, it can also be filtered through a short layer of silica gel (removal of the pyridine catalyst) and then be directly crystallized. The yields achieved are 80-90%.

It is surprisingly possible to dispense with the chromatographic purification and to employ the crude product directly in the final crystallization.

The invention thus relates further to a process as described in Claim 1, which, after workup, is directly followed by a crystallization.

The crude products obtained in the manner described above already have very high purity. The reactions achieved are notable for very high selectivities. In the case of a reaction temperature of −50° C. it was possible to obtain a selectivity of up to 57:1 (α/β) (see Example 1). The formation of the by-products from exo attack on the double bond is virtually no longer observed (total of impurities of this type: <0.1% in the crude product).

The rhenium content of a compound of the formula I prepared in this way is <<7 ppm (LOD*:7 ppm) (*level of detection; method: ICP-OES). The detectability of amounts less than 7 ppm depends on how large the amount of epothilone derivative there is available for the measurement. A larger amount of epothilone derivative means that a content of less than 7 ppm rhenium is more likely to be detectable.

The occurrence of rhenium in the earth's crust is 0.0004 ppm, according to Rutherford online 2006.

Since the final product of the process of the invention may still contain rhenium, a further aspect of the invention is also a product of the process of the invention which still contains rhenium.

One aspect of the invention is the product of the formula I containing more than 0.0004 ppm rhenium.

In one embodiment, the final product contains >0.0004 ppm to 7 ppm rhenium.

In a further embodiment, the final product contains >0.0004 ppm to 1 ppm rhenium.

One aspect of the invention is the product of the formula I containing rhenium in the range from 0.01 ppm to 30 ppm.

A further aspect of the invention is the product of the formula I containing rhenium in the range from 0.1 ppm to 30 ppm.

In one embodiment, the reaction product contains from 1 ppm up to 30 ppm rhenium.

In a further embodiment, the final product contains ≦7 ppm to 30 ppm rhenium.

In a further embodiment, the final product contains 0.01 ppm to 7 ppm rhenium.

In a further embodiment, the final product contains 0.01 ppm to 1 ppm rhenium.

It has proved advantageous in some cases to employ instead of the relatively pure dialkene II purified by chromatography, also the crude product of this compound II directly in the epoxidation, thus making it possible in an unexpected manner to increase the overall yield of the two stages in total.

The novel process allows the compound of the formula (I) to be prepared in high diastereoselectivity and yield and purity. The process is simple to operate and permits scaling-up into the multi-kg range. It has the great advantage beside the methods described in the prior art that no valuable substance is lost through attack on the exo double bond. This process is therefore to be categorized as a very practicable and economically valuable method.

The following examples serve to illustrate the subject-matter of the invention in more detail without intending to restrict it thereto:

EXAMPLE 1

1.000 kg of dialkene of the formula II (prepared according to WO 00/66589), 14.17 g (3 mol %) of methyl-trioxorhenium and 35.5 g (18 mol. %) of 4-cyanopyridine are dissolved in 10 litres of dichloromethane and then cooled to −50° C. 579 ml of 30% strength aqueous hydrogen peroxide solution (3 eq.) are added, and the mixture is stirred at −50° C. for about 70 hours. The reaction is followed by HPLC towards the end. Once precursor (compound of the formula II) is below 1%, the reaction is quenched by adding 580 ml of 20% strength aqueous sodium thiosulphate solution. This is followed by addition of a further 7000 ml of thiosulphate solution and warming to +10° C. The mixture is stirred at +10° C. for one hour, the organic phase is separated off, and the aqueous phase is back-extracted with 5000 ml of dichloromethane. The combined organic phases are washed 5000 ml of saturated aqueous sodium chloride solution. The organic phase is concentrated in vacuo. The residue is filtered through a layer of silica gel (mobile phase: dichloromethane/ethyl acetate gradient).

Yield: 877 g (85% of theory, α/β57:1) of the compound of the formula (I)

Recrystallization from hexane/toluene results in 824.3 g (80% of theory based on II) of colourless crystals.

HPLC purity (100% method): 100%, no impurities>0.05% are detected. The β isomer has been completely removed Rhenium content: <<7 ppm (LOD: 7 ppm)

Elemental Analysis:

Calc. C, 66.27%; H, 7.60%; N, 2.58%; S, 5.90%.

Found C, 66.19%; H, 7.71%; N, 2.54%; S, 5.85%.

Rotation:

$[alpha]_D^{20}$: −73.2° (c=0.514, $CHCl_3$).

$^1$H NMR (300 MHz, $CDCl_3$) delta=0.98 (3H), 1.02 (3H), 1.23 (3H), 1.25-1.78 (7H), 1.31 (3H), 2.15-2.31 (3H), 2.44-2.68 (4H), 2.84 (3H), 2.91 (1H), 3.60 (1H), 3.70 (1H), 4.20 (1H), 4.40 (1H), 5.01 (1H), 5.06 (1H), 5.73 (1H), 6.19 (1H), 7.36 (1H), 7.82 (1H), 7.94 (1H) ppm.

$^{13}$C NMR (300 MHz, $CDCl_3$) delta=219.7 (s, C-9), 170.5 (s, C-5), 168.2 (s, C-aryl), 153.5 (s, C-aryl), 137.2 (s, C-aryl), 135.8 (d, =CH-allyl), 135.3 (s, C-aryl), 122.7 (d, C-aryl), 121.7 (d, C-aryl), 119.7 (d, C-aryl), 117.1 (t, =$CH_2$-allyl), 77.0 (d, C-11), 74.3 (d, C-3), 74.3 (d, C-7), 60.9 (s, C-16), 60.0 (d, C-1), 52.2 (s, C-8), 51.3 (d, C-10), 38.6 (t, C-6), 34.8

(d, C-12), 34.3 (t, C-2), 34.1 (t, CH$_2$-allyl), 31.3 (t, C-15), 29.6 (t, C-13), 22.5 (q, CH$_3$ on C-8), 22.1 (t, C-14), 22.1 (q, CH$_3$ on C-16), 20.2 (q, CH$_3$-aryl), 19.2 (q, CH$_3$ on C-8), 17.9 (q, CH$_3$ on C-12) ppm.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosures of all applications, patents and publications, cited herein and of corresponding German application No. 10 2007 016 046.3, filed Mar. 30, 2007 are incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A process for preparing the epothilone derivative of the formula (I)

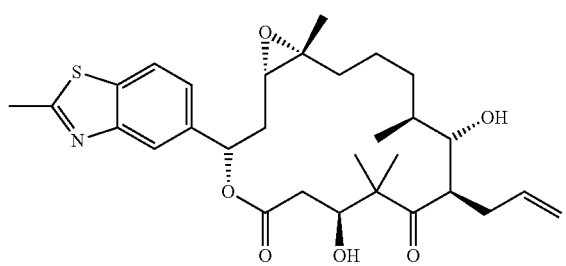

(I)

comprising epoxidizing a dialkene of formula (II)

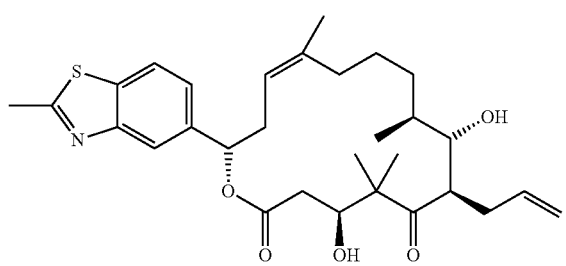

(II)

using methyltrioxorhenium with an epoxidizing agent in an aprotic solvent at −60° C. to −20° C.

2. The process according to claim 1, in which the epoxidizing agent is aqueous hydrogen peroxide solution.

3. The process according to claim 1, further comprising adding of a substituted pyridine derivative.

4. The process according to claim 3, comprising reacting the dialkene of formula (II) at −60 to −20° C. in chlorinated hydrocarbons or mixtures thereof with low-boiling alkanes or toluene or trifluorotoluene as solvent
using 6-36 mol % of a substituted pyridine,
and 1-7 mol % methyltrioxorhenium
and 2-5 equivalents of 10-60% strength aqueous hydrogen peroxide solution.

5. The process according to claim 1, where the reaction times are between 20-120 h.

6. The process according to claim 1, where the concentration of the compound of the formula II is in the range from 1 g in 5 ml of solvent to 1 g in 50 ml of solvent.

7. The process according to claim 1, wherein the solvent is dichloromethane, 1,2-dichloroethane, chloroform, or mixtures thereof with pentane, hexane, heptane, cyclohexane, toluene or trifluorotoluene, or toluene or trifluorotoluene alone.

8. The process according to claim 3, wherein the substituted pyridine is

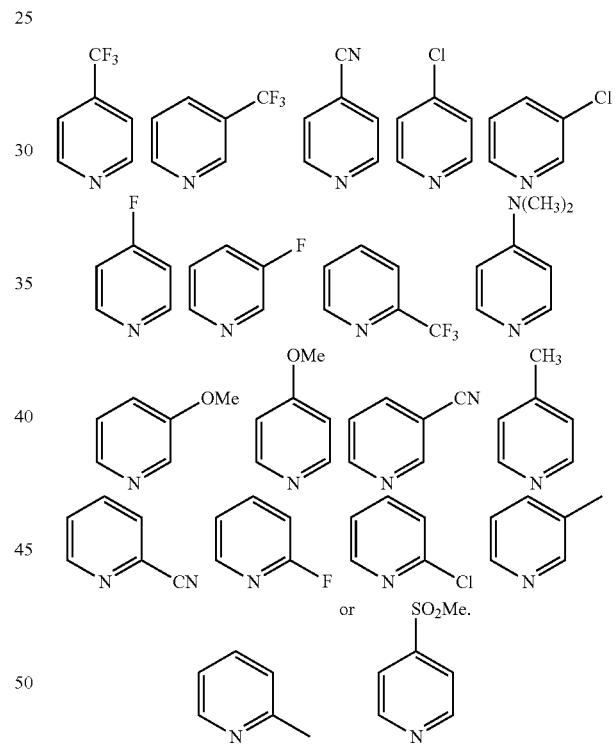

9. The process according to claim 3, wherein the substituted pyridine is an electron-poor pyridine compound which is substituted in position 4 by CN, Br, Cl, F, CF$_3$, SO$_2$(C$_1$-C$_4$) alkyl, SO$_2$NH$_2$, SO$_2$N[(C$_1$-C$_4$)alkyl]$_2$, COOH or COO(C$_1$-C$_4$)alkyl.

10. The process according to claim 1, wherein the crude product obtained is crystallized.

* * * * *